(12) United States Patent
Bailey-Jackson

(10) Patent No.: US 9,198,435 B2
(45) Date of Patent: Dec. 1, 2015

(54) NATURAL PESTICIDE COMPOSITION AND METHOD OF PRODUCING

(71) Applicant: Sharon Bailey-Jackson, Brooklyn, NY (US)

(72) Inventor: Sharon Bailey-Jackson, Brooklyn, NY (US)

(*) Notice: Subject to any disclaimer, the term of this patent is extended or adjusted under 35 U.S.C. 154(b) by 36 days.

(21) Appl. No.: 14/273,995

(22) Filed: May 9, 2014

(65) Prior Publication Data

US 2015/0086656 A1 Mar. 26, 2015

Related U.S. Application Data

(60) Provisional application No. 61/880,328, filed on Sep. 20, 2013.

(51) Int. Cl.
| | | |
|---|---|---|
| *A01N 65/00* | (2009.01) | |
| *A01N 65/16* | (2009.01) | |
| *A01N 65/22* | (2009.01) | |
| *A61K 36/00* | (2006.01) | |
| *A01N 65/40* | (2009.01) | |

(52) U.S. Cl.
CPC ............... *A01N 65/16* (2013.01); *A01N 65/22* (2013.01); *A01N 65/40* (2013.01); *A61K 36/00* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 4,376,784 A | 3/1983 | Harney |
| 2010/0196520 A1 | 8/2010 | Elraz |
| 2011/0229589 A1 | 9/2011 | Elraz |
| 2013/0142893 A1 | 6/2013 | Bessette |
| 2013/0156839 A1 | 6/2013 | Messina |

*Primary Examiner* — Michael Meller
(74) *Attorney, Agent, or Firm* — Daniel Boudwin; Global Intellectual Property Agency LLC

(57) ABSTRACT

The invention disclosed herein is directed to a natural pesticide composition and the method for producing such a composition. The composition comprises a mixture of distilled water, isopropyl alcohol, rosemary oil, rosemary extract, wintergreen oil, and garlic. The composition includes organic and natural materials and is capable of repelling and destroying pests such as insects and parasites. The extract and oil from the herbs and the garlic can externally release a repelling agent to discourage the pests and the alcohol dehydrates the insects. The present invention provides a natural eco-friendly pesticide that is safe for use on plants, as well as animals and people alike.

1 Claim, No Drawings

NATURAL PESTICIDE COMPOSITION AND METHOD OF PRODUCING

CROSS REFERENCE TO RELATED APPLICATION

This application claims the benefit of U.S. Provisional Application No. 61/880,328 filed on Sep. 20, 2013. The above identified patent application is herein incorporated by reference in its entirety to provide continuity of disclosure.

BACKGROUND OF THE INVENTION

1. Field of the Invention

The present invention relates to a natural pesticide composition and method. More specifically, the present invention pertains to a safe, green, natural eco-friendly pesticide and method of making the same, which destroys insects, parasites, or other organisms harmful to cultivated plants or to animals and humans.

Pesticides are chemical substances that deter, incapacitate, kill, or otherwise discourage any pests from coming in contact with the covered object. Target pests can include insects, parasites, plant pathogens, weeds, mollusks, birds, fish, nematodes, and microbes that destroy property and cause nuisance, spread disease, or are disease vectors. The most common use of pesticides is as plant protection products to increase agricultural productivity, which in general protect plants from weeds, plant diseases, or insects. Additionally, pesticides are used in medicine, industry, and by many consumers. Although pesticides have many benefits, pesticide use raises a number of environmental concerns. For instance, nearly all pesticides have the potential to significantly alter ecosystems. Pesticides may also reach water, air, and soil and cause pollution and contamination.

Additionally, many pesticides are toxic to humans and may cause acute and delayed health effects to those who are exposed. Exposure to pesticides is known to cause a variety of adverse health effects, ranging from simple irritation of the skin and eyes to more severe effects such as negatively impacting the nervous system, damaging reproductive organs, and causing cancer.

The present invention provides an insect repellant composed of natural ingredients. The composition consists essentially of 70% isopropyl alcohol, wintergreen oil, rosemary extract, organic rosemary oil, and two large aged garlic bulbs in a distilled water solvent. The composition can be sprayed on a desired area to repel and destroy various types of pests, including insects and parasites. The primary advantage of the present invention is not only its composition of natural, organic ingredients, but more specifically its process of synthesis. The miscibility of isopropyl alcohol eliminates the need to use additives such as emulsifiers. Additionally, the process eliminates the need to stimulate the mixture of the ingredients over extreme temperatures and conditions. In this way, the method of the present invention increases the yield of desired composition.

2. Description of the Prior Art

Devices have been disclosed in the prior art that relate to insect repellant compositions. These include devices that have been patented and published in patent application publications. Some of these patents describe a composition of rosemary oil and at least one diluent selected from the group consisting of various essential oils, lecithin, benzyl alcohol, cintronellal, and d-limonene. Another patent describes an insect repellent solution comprising a combination of at least two essential oils, citrus peel tincture, and vinegar. These formulations and methods of producing the same, however, are costly and difficult to synthesize. The following is a list of formulations deemed most relevant to the present disclosure, which are herein described for the purposes of highlighting and differentiating the unique aspects of the present invention, and further highlighting the drawbacks existing in the prior art.

For example, U.S. Published Patent Application Number 2013/0142893 to Bessette discloses pesticidal compositions containing rosemary oil and/or wintergreen oil and methods for using the same. The pesticidal compositions comprise rosemary oil and at least one diluent selected from a group of wintergreen oil, peppermint oil, mineral oil, phenyl ethyl propionate, lecithin, benzyl alcohol, citronellal, d-limonene, safflower oil, soybean oil, and sesame oil. The pesticidal composition of Bessette is primarily used against fungus, bacterial, insects, arachnids, larvae, and larvae eggs. Though Bessette discloses use of plant essential oils to be used against invertebrate pests, Bessette does not disclose the use of garlic bulbs. The present invention comprises garlic bulbs that produce a repelling agent to discourage insects. Additionally, the pesticidal compositions of Bessette utilize synthetic versions of plant essential oils that may contain toxins such as pesticides, fertilizers, or carrier oils. In contrast, the present invention utilizes organically grown plants, thereby providing a better alternative to an existing pest repellent to the user.

U.S. Published Patent Application Number 2010/0196520 to Elraz ("Elraz '520") discloses an insect repellent solution comprising a combination of at least two essential oils with an emulsifier and citrus peel tincture, and vinegar. The formulation is prepared by mixing the essential oils with an emulsifier and citrus tincture, and adding the mixture to distilled water at a temperature of 40° C. so that the final volume of water is 90% and the final volume of vinegar and oil mixture are each 5%. The formulation is thereafter mixed for approximately 2 hours using a mechanical stirrer. While the formulation of Elraz '520 combines active ingredients possessing repelling effects on insects, the active ingredients are normally immiscible and require an emulsifier to stabilize the formulation. In contrast, the present invention does not require an emulsifier to encourage the suspension of one ingredient in another. Additionally, the present invention does not require an extensive stirring.

Similarly, U.S. Published Patent Application Number 2011/0229589 to Elraz ("Elraz '589") also provides an insect repellent solution comprising vinegar and a combination of at least two essential oils. More specifically, Elraz '589 discloses formulation comprising tee tree oil, vinegar, and essential oil selected from a group of citronella, rosemary oil, lemon grass oil, and neem oil. The formulation further comprises an emulsifier in an amount of up to about 10% volume per volume. The emulsifier is mixed with a combination of essential oils before being added to water and vinegar. The mixture is stirred for about 2 hours at ambient temperatures using a mechanical stirrer. Thereafter, the mixture is rested for approximately 24 to 72 hours prior to use. While the formulation of Elraz '589 combines active ingredients possessing repelling effects on insects, the active ingredients do not include garlic bulbs. In contrast, the present invention utilizes a distilled water solvent containing strong organic garlic extract. Additionally, the present invention does not require an emulsifier or extensive stirring to combine the ingredients.

Another device, U.S. Published Patent Application Number 2013/0156839 to Messina discloses geraniol oil-based formulations which may be applied to various surfaces to deter wildlife pests. The geraniol oil-based formulations further comprise mint oil, caster oil, sodium lauryl sulfate, kaolin, and xanthan gum. Although geraniol oil is known for use in plant based mosquito repellents, it is commonly used in perfumes and in flavors such as peach, raspberry, and grapefruit, among other flavors. As such, bees and other insects can associate the geranoil oil scent with nectar-bearing flowers, which can attract bees and other insects rather than repelling them. In contrast, the composition of the present invention is not made attractive to pests. The pesticide composition of the present invention comprises herb oils and garlic that produce powerful odor that repels pests. As such, the present invention deters, incapacitates, kills, or otherwise discourages any pests in unwanted areas.

Finally, U.S. Pat. No. 4,376,784 to Harney discloses pesticidal esters of pyrethrin or pyrethroid type in which the methylene group bonded to the ester carbonyl and/or ester oxygen bears a fluorine substituent. While the pesticidal esters of pyrethrin or pyrethroid type disclosed in Harney are very toxic to wide varieties of insect and other invertebrate pests, the esters are costly and difficult to synthesize. Moreover, the difficulty in deriving ester derivatives which contain a fluoro substituted methylene group $\alpha$- to the ester carbonyl and/or $\alpha$- to the ester oxygen results in an unpredictable yield of the desired product. In contrast, the present invention provides a method of producing a natural pesticide composition that is easy to control. Thus, the method of the present invention yields desired product with no contamination and no unpredictable yield.

These prior art devices have several known drawbacks. The present invention discloses oil based pesticide composition, which contain a mixture of alcohol, water, plant oil, plant extract, and garlic. The formulation of such pesticide makes such composition effective for deterring and killing a wide variety of pests. Moreover, the preparation of such composition does not require extensive synthesis of each of the ingredients, prolonged period of stirring, or exposure to extreme temperatures. Accordingly, the method of production of the pesticide composition of the present invention is consistent from batch to batch, thus resulting in invariable performance for killing pests.

It is therefore submitted that the present invention substantially diverges in design elements from the prior art, which overcomes the disadvantages of the prior art devices, and consequently it is clear that there is a need in the art for an improvement to existing insect repellant compositions. In this regard the instant invention substantially fulfills these needs.

SUMMARY OF THE INVENTION

In view of the foregoing disadvantages inherent in the known types of insect repellant compositions now present in the prior art, the present invention provides a new improvement to a natural pesticide composition wherein the same can be utilized for deterring, incapacitating, killing, or otherwise discouraging any pests such as insects and parasites.

It is therefore an object of the present invention to provide a new and improved natural pesticide composition that has all of the advantages of the prior art and none of the disadvantages.

It is another object of the present invention to provide a new and improved pesticide composition that comprises natural and organic ingredients.

Another object of the present invention is to provide a new and improved natural pesticide composition that is free of common skin and respiratory irritants such as dyes and synthetic fragrances.

Yet another object of the present invention is to provide a new and improved natural pesticide composition that is readily biodegradable and made from renewable sources.

Still yet another object of the present invention is to provide a new and improved natural pesticide composition that is safe for waterways and marine life.

Still yet another object of the present invention is to provide a new and improved natural pesticide composition wherein the method of producing the same is easy to control.

Other objects, features and advantages of the present invention will become apparent from the following detailed description.

DETAILED DESCRIPTION OF THE INVENTION

For the purposes of presenting a brief and clear description of the present invention, the preferred embodiment will be discussed as used for utilized for deterring, incapacitating, killing, or otherwise discouraging any pests such as insects and parasites.

The pesticidal composition of the present invention is an aqueous solution comprising water, 70% isopropyl alcohol, rosemary extract, rosemary oil, wintergreen oil, and garlic bulbs. In a preferred embodiment, distilled water is used as a solvent to increase purity of the composition, wherein the distilled water comes from recondensed steam. The purification process includes boiling water and collecting water vapors that return to its liquid state from gaseous state. This process causes impurities to separate from the water. Alternatively, filtered water may be used, wherein one of many different methods of filtration may be used to separate impurities from the water. The preferred embodiments of the present invention is provided in Table 1.

TABLE 1

| | Preferred Concentration Range | |
|---|---|---|
| Ingredient | Amount v/v Range Minimum | Amount v/v Range Maximum |
| Water | 15.86% | 20.32% |
| 70% Isopropyl Alcohol | 74.82% | 79.31% |
| Rosemary Extract | 0.40% | 0.57% |
| Rosemary Oil | 0.40% | 0.57% |
| Wintergreen Oil | 4.01% | 4.02% |
| Garlic | <0.01% | <0.01% |

The active ingredient within the composition, isopropyl alcohol, is used widely as a solvent and as a strong, but safe cleaning fluid. Isopropyl alcohol is miscible in water, and it will dissolve many oils. It is preferred that the isopropyl alcohol is 70% alcohol in water. Isopropyl alcohol is prepared via three different methods: indirect hydration of propylene; direction hydration of propylene; and catalytic hydrogenation of acetone. In the indirect hydration process, propylene is reacted with sulfuric acid to produce mono- and diisopropyl sulfates, which are then hydrolysed to isopropanol. In the two step strong acid process, separate reactors are used for the propylene-absorption phase and the hydrolysis of the sulfate esters. The reaction occurs at high sulfuric acid concentration (>80% by weight) and low temperature (20-30° C.). The weak acid process is conducted in a single step at lower acid concentration (60%-80% by weight) and higher temperature (60-65° C.).

When sprayed directly onto pests, 70% isopropyl alcohol dehydrates and kills pests by absorbing water through the exoskeleton of the pests by osmosis. Accordingly, increasing the volume percentage of 70% isopropyl alcohol increases the effective strength of the pesticidal composition of the present invention. Conversely, the volume percentage of 70% isopropyl alcohol may be reduced to create a milder composition. The total concentrations of all of the ingredients in the decreased and increased strength embodiments of the present invention are provided in Table 2.

TABLE 2

Composition Strength

| Ingredient | Amount v/v Decreased Strength | Amount v/v Increased Strength |
|---|---|---|
| Water | 21.80% | 14.70% |
| 70% Isopropyl Alcohol | 72.67% | 80.83% |
| Rosemary Extract | 0.61% | 0.37% |
| Rosemary Oil | 0.61% | 0.37% |
| Wintergreen Oil | 4.30% | 3.73% |
| Garlic | <0.01% | <0.01% |

Rosemary extract is produced from *Rosmarinus officinalis* or *Rosmarinus coronarium* of the Labiatae family. Rosemary is rich in antioxidant and anti-inflammatory agents. Rosemary extract has been used commercially as a food preservative because it improves the shelf life and heat stability of oils. Accordingly, rosemary extract helps prolong the shelf life of the present invention. It is preferred that rosemary extract is produced by steeping organically grown rosemary needles in an alcohol solvent, such as 70% isopropyl alcohol, for at least six weeks, with the rosemary needles/alcohol ratio being 1:2 by weight. Then, the needles are drained and the remaining liquid is preserved. Alternatively, the extract may be made by diluting rosemary oil in 70% isopropyl alcohol to a desired strength. For instance, rosemary oil may be diluted in alcohol, with the rosemary oil/alcohol ratio being 1:3 by volume. Accordingly, in some embodiments, diluted rosemary oil may be substituted for rosemary extract. The formulation of this embodiment is provided in Table 3.

TABLE 3

Rosemary Extract Substitution

| Ingredient | Amount v/v Range Minimum | Amount v/v Range Maximum |
|---|---|---|
| Water | 15.89% | 20.38% |
| 70% Isopropyl Alcohol | 74.84% | 79.54% |
| Rosemary Extract | 0.00% | 0.00% |
| Rosemary Oil | 0.54% | 0.77% |
| Wintergreen Oil | 4.02% | 4.03% |
| Garlic | <0.01% | <0.01% |

Similarly, rosemary oil is preferably extracted directly from a rosemary plant. Rosemary oil is much more concentrated and intense than the extracts. Rosemary oil has a clear, powerful herbal smell, and is clear in color and watery in viscosity. It is desired to use a Grade A pure therapeutic quality oil that is derived from an organically grown plant distilled at the proper temperatures using steam distillation. Grade B food grade quality rosemary oil may be used, however. The main chemical components of rosemary oil include, without limitation, a-pinene, borneol, b-pinene, camphor, bornyl acetate, camphene, 1,8-cineole and limonene. In some embodiments, rosemary oil may be substituted with a higher concentration of rosemary extract, as provided in Table 4.

TABLE 4

Rosemary Oil Substitution

| Ingredient | Amount v/v Range Minimum | Amount v/v Range Maximum |
|---|---|---|
| Water | 13.55% | 20.32% |
| 70% Isopropyl Alcohol | 67.06% | 73.38% |
| Rosemary Extract | 1.37% | 2.29% |
| Rosemary Oil | 0.00% | 0.00% |
| Wintergreen Oil | 3.44% | 4.01% |
| Garlic | <0.01% | <0.01% |

Wintergreen oil is extracted from the leaves and bark of *Gaultheria Procumbens* by cold pressing or by steam distillation of the leaves of the plant following maceration in warm water. The main chemical components of the wintergreen oil include, without limitation, birch oil, methyl salicylate, a-pinene, myrcene, δ-3-carene, limonene, 3,7-guaiadiene, and δ-cadiene. The wintergreen oil may be Grade A pure therapeutic quality or Grade B food grade quality. It is preferred, however, to use a Grade A quality oil is used as the purpose and intent of the present invention is to use a natural ingredient in purest form.

Garlic is a powerful natural insect repellent that is biodegradable and does not pollute the environment. It is a natural extract and does not affect insects that are beneficial to landscapes. Garlic bulbs contain an amino acid that converts to allicin when it undergoes a physical change, such as crushing, cutting, or soaking. The characteristic odor released as a result of this process has powerful properties. When garlic extract is absorbed by a plant, biochemical changes take place in its foliage which cause it to actively repel insects. However, the treatment is substantially odorless to humans within minutes of application. Insects are naturally repulsed by the presence of the botanical extract. Therefore, insects do not build up a resistance to garlic treatments. Garlic can also be applied to many sensitive trees, shrubs, and turf that traditional treatments would harm. Additionally, garlic is safe for topical application.

A method for producing the natural pesticide composition of the present invention includes the steps of placing two bulbs of organic garlic in a cleansing bath to remove dirt and byproducts from the surface of the garlic bulb. This is generally accomplished with a distilled water bath, in which the garlic bulbs are submerged within the water. The water bath is then inspected for clarity thereafter. If the water exhibits discoloration or floating debris, the garlic bulbs are removed and placed in a further water bath, and so on until the water is clear and with no floating debris from the garlic bulbs. This process thoroughly cleans the garlic bulbs. Though the weight of each garlic bulb may vary, it is preferred that each garlic bulb is approximately 28.5 grams in weight.

After cleaning the garlic bulbs, they are submerged in 120 to 180 milliliters of distilled water in a clean glass container with a cover. Thereafter, the garlic solution is covered and refrigerated for approximately 24 hours at approximately 1° to 4° C. This process initiates the aging process of garlic and creates a raw garlic extract. Once the garlic bulbs have been soaked for the allotted time, the solution is brought back to ambient temperatures of approximately 17° to 23° C. It is preferred, however, that the ambient temperature is 20° C. Thereafter, 600 to 650 milliliters of 70% isopropyl alcohol, three to five milliliters of rosemary oil, three to five milliliters of rosemary extract, and 30 to 35 milliliters of wintergreen oil are added to the garlic solution. The ingredients can be mixed together and aged for approximately 48 to 50 hours at ambient temperatures of approximately 17° to 23° C. In a preferred embodiment, however, that the composition is aged at approximately 20° C.

When the composition is complete, the composition is poured into a spray bottle and sealed to prevent air leakage. It is preferred, however, that the composition is strained using a fine mesh strainer to rid of pieces of the garlic bulbs before it is poured into the spray bottle to prevent clogging. The composition can be sprayed directly onto pests such as insects and parasites without harming people and the surrounding environment. The pesticidal composition of the present invention has been shown to preserve without refrigeration in excess of twelve months without loss of effectiveness of the fluid. The present invention is safe when applied topically.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A spray bottle consisting essentially of 70% isopropyl alcohol in an amount from about 67% to 81% by volume, rosemary oil in an amount of about 0.8% by volume, wintergreen oil in an amount from about 3.4% to 4.4% by volume and a garlic bulb extract.

* * * * *